United States Patent
Zeng et al.

(10) Patent No.: US 9,718,027 B2
(45) Date of Patent: Aug. 1, 2017

(54) METHOD AND SYSTEM FOR MITIGATING UREA DEPOSITS WITHIN AN SCR CATALYST SYSTEM

(71) Applicant: Cummins IP, Inc., Columbus, IN (US)

(72) Inventors: Fan Zeng, Columbus, IN (US); C. Larry Bruner, Greenwood, IN (US); Edmund P. Hodzen, Columbus, IN (US); Ian A. Package, Columbus, IN (US); Shankar Kumar, Columbus, IN (US); Krishna Kamasamudram, Columbus, IN (US)

(73) Assignee: Cummins IP, Inc., Columbus, IN (US)

( * ) Notice: Subject to any disclaimer, the term of this patent is extended or adjusted under 35 U.S.C. 154(b) by 14 days.

(21) Appl. No.: 14/808,124

(22) Filed: Jul. 24, 2015

(65) Prior Publication Data

US 2015/0328586 A1 Nov. 19, 2015

Related U.S. Application Data

(63) Continuation of application No. 13/549,324, filed on Jul. 13, 2012, now Pat. No. 9,091,189.

(51) Int. Cl.
*G01N 35/08* (2006.01)
*B01D 53/94* (2006.01)
(Continued)

(52) U.S. Cl.
CPC ..... *B01D 53/9495* (2013.01); *B01D 53/9404* (2013.01); *F01N 3/2066* (2013.01);
(Continued)

(58) Field of Classification Search
None
See application file for complete search history.

(56) References Cited

U.S. PATENT DOCUMENTS 6,833,272 B1 12/2004 Binder et al.
8,061,123 B2 11/2011 Driscoll et al.
(Continued)

FOREIGN PATENT DOCUMENTS

GB 2 435 625 9/2007
WO WO-2010/088208 8/2010

OTHER PUBLICATIONS

International Search Report for International Application No. PCT/US2013/050504, dated Nov. 14, 2013, 2 pages.

*Primary Examiner* — Robert Xu
(74) *Attorney, Agent, or Firm* — Foley & Lardner LLP (57) ABSTRACT

A method and system for mitigating a urea deposit within an SCR system that includes determining a mass of an accumulated urea deposit present within the SCR catalyst and SCR piping, comparing the mass of the accumulated urea deposit with a deposit upper threshold limit, and initiating an SCR regeneration event when the mass of the accumulated urea deposit is greater than the deposit upper threshold limit. The method further includes determining an amount of $NH_3$ passing through the SCR catalyst downstream of the urea deposit, comparing the amount of $NH_3$ passing through the SCR catalyst with an $NH_3$ regeneration threshold limit, and terminating the SCR regeneration event when the level of $NH_3$ passing through the SCR catalyst is less than the SCR $NH_3$ regeneration threshold.

12 Claims, 6 Drawing Sheets

(51) Int. Cl.
*G01N 33/00* (2006.01)
*F01N 3/20* (2006.01)
*F01N 9/00* (2006.01)

(52) U.S. Cl.
CPC ........... *F01N 9/00* (2013.01); *G01N 33/0054* (2013.01); *F01N 2560/021* (2013.01); *F01N 2610/1493* (2013.01); *F01N 2900/1616* (2013.01); *F01N 2900/1806* (2013.01); *Y02T 10/24* (2013.01); *Y02T 10/47* (2013.01); *Y10T 436/12* (2015.01)

(56) References Cited

U.S. PATENT DOCUMENTS

| | | |
|---|---|---|
| 8,627,651 B2 | 1/2014 | Ponnathpur |
| 2008/0271440 A1 | 11/2008 | Xu et al. |
| 2010/0122525 A1 | 5/2010 | Fujita et al. |
| 2011/0030343 A1 | 2/2011 | Kiser et al. |
| 2011/0131958 A1 | 6/2011 | Adelman et al. |
| 2011/0167805 A1 | 7/2011 | Chen |

METHOD AND SYSTEM FOR MITIGATING UREA DEPOSITS WITHIN AN SCR CATALYST SYSTEM

CROSS-REFERENCE TO RELATED APPLICATIONS

The present application is a continuation of U.S. patent application Ser. No. 13/549,324, entitled "Method and System For Mitigating Urea Deposits Within an SCR Catalyst System," filed on Jul. 13, 2012, which is currently co-pending and incorporated by reference in its entirety and for all purposes.

FIELD

This disclosure relates to controlling nitrogen oxides ($NO_x$) emissions for internal combustion engines, and more particularly to apparatus, systems and methods for estimating and mitigating urea deposits for a selective catalytic reduction (SCR) catalyst system.

BACKGROUND

Emissions regulations for internal combustion engines have become more stringent over recent years. Environmental concerns have motivated the implementation of stricter emission requirements for internal combustion engines throughout much of the world. Governmental agencies, such as the Environmental Protection Agency (EPA) in the United States, carefully monitor the emission quality of engines and set acceptable emission standards, to which all engines must comply. Consequently, the use of exhaust after-treatment systems on engines to reduce emissions is increasing.

Generally, emission requirements vary according to engine type. Emission tests for compression-ignition (diesel) engines typically monitor the release of carbon monoxide (CO), unburned hydrocarbons (UHC), diesel particulate matter (PM) such as ash and soot, and nitrogen oxides ($NO_x$). Diesel oxidation catalysts (DOC) have been implemented in exhaust gas after-treatment systems to oxidize at least some particulate matter in the exhaust stream and to reduce the unburned hydrocarbons and CO in the exhaust to less environmentally harmful compounds. To remove the diesel particulate matter, a diesel particulate matter filter, or PM filter, is typically installed downstream from the DOC or in conjunction with the DOC.

A common PM filter comprises a porous ceramic matrix with parallel passageways through which exhaust gas passes. Particulate matter subsequently accumulates on the surface of the filter, creating a buildup which must eventually be removed to prevent obstruction of the exhaust gas flow. The common forms of particulate matter are ash and soot. Ash, typically a residue of burnt engine oil, is substantially incombustible and builds slowly within the filter. Soot, chiefly composed of carbon, results from incomplete combustion of fuel and generally comprises a large percentage of particulate matter buildup. Various conditions, including, but not limited to, engine operating conditions, mileage, driving style, terrain, etc., affect the rate at which particulate matter accumulates within a diesel particulate filter. Accumulation of particulate matter in the PM filter causes backpressure to build within the exhaust system. Excessive backpressure on the engine can degrade engine performance (e.g., lower power and efficiency), and in some cases may result in engine stall.

Particulate matter, in general, oxidizes in the presence of nitric oxides (particularly $NO_2$) at modest temperatures, or in the presence of oxygen at higher temperatures. If too much particulate matter has accumulated when oxidation begins, the oxidation rate may get high enough to cause an uncontrolled high-temperature excursion. The resulting heat can destroy the filter and damage surrounding structures. Recovery can be an expensive process. To prevent potentially hazardous situations, accumulated particulate matter is commonly oxidized and removed in a controlled regeneration process before excessive levels have accumulated.

For oxidation of the accumulated particulate matter, exhaust gas temperatures generally must exceed the temperatures typically reached at the filter inlet. Consequently, additional methods to initiate regeneration of a diesel particulate filter may be used. In one method, a reactant, such as diesel fuel, is introduced into an exhaust after-treatment system to increase the temperature of the exhaust gases entering filter and initiate oxidation of particulate buildup. A PM filter regeneration event occurs when substantial amounts of soot are consumed on the PM filter.

A controlled PM filter regeneration can be initiated by the engine's control system when a predetermined amount of particulate has accumulated on the filter, when a predetermined time of engine operation has passed, or when the vehicle has driven a predetermined number of miles. Controlled or active PM filter regeneration typically consists of driving the filter temperature up to $O_2$ oxidation temperature levels for a predetermined time period such that oxidation of soot accumulated on the PM filter takes place.

With regard to reducing $NO_x$ emissions, $NO_x$ reduction catalysts, including selective catalytic reduction (SCR) systems, are utilized to convert $NO_x$ (NO and $NO_2$ in some fraction) to $N_2$ and other compounds. SCR systems utilize a reductant, typically ammonia, to reduce the $NO_x$. Currently available SCR systems can produce high $NO_x$, conversion rates allowing the combustion technologies to focus on power and efficiency. However, currently available SCR systems also suffer from a few drawbacks.

SCR systems utilize a spray dosing system to introduce ammonia reductant into the exhaust stream upstream of the SCR catalyst. When just the proper amount of ammonia is available at the SCR catalyst under the proper conditions, the ammonia is utilized to reduce $NO_x$. However, if the reduction reaction rate is too slow, or if excess ammonia is introduced into the exhaust stream upstream of the SCR catalyst, the surplus ammonia can slip through the SCR without being utilized in the catalytic reaction. Because ammonia is an extreme irritant and an undesirable emission, ammonia slips of even a few tens of ppm are problematic. As a result, an additional ammonia oxidation (AMOX) catalyst may be installed downstream of the SCR catalyst to capture and oxidize any residual ammonia components in the exhaust stream into more benign compounds prior to being released into the atmosphere.

Due to the undesirability of handling pure ammonia, many systems utilize an alternate solution, such as aqueous urea, that vaporizes and decomposes to ammonia in the exhaust stream. However, the decomposition of urea into ammonia can be highly dependent upon the temperature of the exhaust gas. If the temperature of the exhaust gas is too low, for example, some of the vaporized urea can condense onto the interior surfaces of the SCR system piping and the SCR catalyst bed and crystalize into urea deposits, which can build over time.

Like the build-up of particulate matter in the PM filter, the urea deposits in the SCR system may also have negative impacts on the operation of the internal combustion engine. For instance, the deposits may restrict the flow passages of the exhaust stream, causing higher back-pressures and reducing engine and after-treatment system performance and efficiency. The deposits may also disrupt the flow and mixing of the urea reductant into the exhaust stream and thereby reduce the decomposition into ammonia ($NH_3$) with a subsequent drop in $NO_x$ reduction efficiency. Moreover, the re-direction of a portion of the injected urea into the urea deposits can also reduce the amount of urea reductant which was intended to reach the SCR catalyst, making control of the SCR system more difficult and further reducing $NO_x$ reduction efficiency.

Similar to the periodic controlled oxidation or regeneration of the PM filter to remove an excess accumulation of particulate matter, an increase in the temperature of the exhaust gases entering the SCR system can release and decompose the urea deposits into ammonia for utilization or storage in the SCR catalyst. However, if the urea deposits have been allowed to grow too large, the additional surge of ammonia can be in excess of the amount which can be effectively utilized in the ongoing catalytic reaction or captured and stored in the SCR catalyst, and thus will escape the SCR system as ammonia slip. In addition, the repeated cycling of the SCR system inlet temperature to temperature levels sufficient to release and decompose the urea deposits into ammonia can both reduce the efficiency of the ongoing SCR reaction as well as cause premature wear and degradation of the SCR catalyst components, and should be limited as much as possible.

Also, many known SCR systems do not utilize an ammonia oxidation (AMOX) catalyst downstream of the SCR catalyst to convert at least some ammonia slipping from the SCR catalyst to $N_2$ and other less harmful compounds. For those conventional SCR systems that do not include an AMOX catalyst, the operating conditions and conversion capability of the AMOX catalyst are not factored into the reductant dosing rate, ammonia storage control, ammonia slippage control, and $NO_x$ conversion efficiency feedback of such systems. However, these conventional AMOX-less SCR systems are still required to comply with the stringent emission requirements for internal combustion engines, and must meet these standards through different means.

SUMMARY

The subject matter of the present application has been developed in response to the present state of the art, and in particular, in response to the problems and needs in the art that have not yet been fully solved by currently available exhaust after-treatment systems. Accordingly, the subject matter of the present application has been developed to provide methods and systems for estimating and mitigating urea deposits within an SCR system that overcomes at least some shortcomings of the prior art after-treatment systems. More specifically, disclosed herein is an improved method and system for determining the build-up of the urea deposits within the SCR system with greater accuracy. In addition, a more capable SCR regeneration control system is described herein that better controls the SCR regeneration process so as to minimize the high inlet temperature regeneration cycles while maintaining the urea deposits to a minimum amount, which helps to avoid any excess ammonia slip during the SCR regeneration cycle.

According to one representative embodiment, a method for mitigating a urea deposit within a selective catalytic reduction (SCR) system that is in exhaust receiving communication with an exhaust gas stream produced by an engine system can include various steps or operations. For example, the method can include determining a mass of an accumulated urea deposit present within the SCR system, comparing the mass of the accumulated urea deposit with a deposit upper threshold limit, and initiating an SCR regeneration event when the mass of the accumulated urea deposit is greater than the deposit upper threshold limit. The method can further include determining an amount of ammonia ($NH_3$) passing through the SCR catalyst downstream of the urea deposit, comparing the amount of $NH_3$ passing through the SCR catalyst with an $NH_3$ regeneration threshold limit, and terminating the SCR regeneration event when the level of $NH_3$ passing through the SCR catalyst is less than the $NH_3$ regeneration threshold limit.

In certain implementations, determining the mass of the accumulated urea deposit includes determining a rate of urea deposit accumulation within the SCR system, determining a first time period, the first time period being the time elapsed from a previous SCR regeneration event, and integrating the rate of urea deposit accumulation within the SCR system over the first time period to calculate the mass of the accumulated urea deposit. The method may also include measuring the flow rate of $NH_3$ passing through the SCR system with an $NH_3$ sensor positioned downstream of the urea deposit. In some implementations, the $NH_3$ sensor is an SCR catalyst $NH_3$ mid-bed sensor.

According to another representative embodiment, a method for mitigating the urea deposit within the selective catalytic reduction (SCR) system can include determining a mass of a urea deposit present within the SCR catalyst, comparing the accumulated mass of the urea deposit with a deposit upper threshold limit, and initiating an SCR regeneration event when the accumulated mass of the urea deposit is greater than the deposit upper threshold limit. The method can also include determining an amount of $NH_3$ passing through the SCR catalyst downstream of the urea deposit, comparing the amount of $NH_3$ passing through the SCR catalyst with an $NH_3$ regeneration threshold limit, and maintaining the SCR regeneration event when the level of $NH_3$ passing through the SCR catalyst is greater than the $NH_3$ regeneration threshold limit. The method can further include comparing the mass of the urea deposit with a deposit lower threshold limit, and terminating the SCR regeneration event when the mass of the decomposing urea deposit is less than the deposit lower threshold limit.

In some implementations, determining the mass of the accumulated urea deposit includes determining a rate of urea deposit accumulation within the SCR system, determining a first time period, the first time period being the time elapsed from a previous SCR regeneration event, and integrating the rate of $NH_3$ passing through the SCR catalyst over the second time period to calculate the amount of $NH_3$ passing through the SCR catalyst. In certain implementations, determining the mass of the accumulated urea deposit includes determining a rate of urea deposit decomposition within the SCR system and integrating the rate of urea deposit decomposition within the SCR system over the second time period to calculate the second estimate of the mass of the accumulated urea deposit.

According to yet another representative embodiment, a system for mitigating a urea deposit within a selective catalytic reduction (SCR) system that is in exhaust receiving communication with an exhaust gas stream produced by an engine system can include various sensor and control system modules. For example, the system can include a reductant delivery system configured to inject reductant into the exhaust gas stream upstream of the SCR catalyst. The system can further include an SCR $NH_3$ sensor that is also in exhaust gas receiving communication with the exhaust gas stream. The SCR $NH_3$ sensor can be located downstream of the accumulated urea deposit.

The system can also include a controller having an SCR catalyst regeneration module that is in electrical communication with each of the reductant delivery system and the SCR $NH_3$ sensor. In turn, the SCR catalyst regeneration module can include a urea deposit accumulation module that is operable to determine a mass of an accumulated urea deposit present within the SCR catalyst from inputs received from the reductant delivery system (which can be a reductant dosing flow signal). The SCR catalyst regeneration module can also include an $NH_3$ slip feedback module that is operable to determine an amount of $NH_3$ passing through the SCR catalyst downstream of the urea deposit from sensor inputs received from the SCR $NH_3$ sensor.

In addition, the SCR catalyst regeneration module may be operable to both initiate an SCR regeneration event when the mass of the accumulated urea deposit is greater than a deposit upper threshold limit, and to terminate the SCR regeneration event when the level of $NH_3$ passing through the SCR catalyst after initiation of the SCR regeneration event is less than an SCR $NH_3$ regeneration threshold.

According to another embodiment, a computer program product that includes a computer readable medium with computer usable program code executable to perform operations for mitigating a urea deposit within an SCR catalyst included within and SCR system. The SCR system is coupled to an internal combustion engine and operable to inject a reductant, such as urea, into an exhaust gas stream. While most of the injected urea reduces to ammonia in the exhaust gas stream and facilitates a reduction of $NO_x$ emissions in the exhaust gas stream within the SCR catalyst, a portion of the reductant can condense and crystalize onto the surfaces of the SCR piping and the SCR catalyst, thereby forming a problematic urea deposit.

The operations of the computer program product can include determining a mass of an accumulated urea deposit present within the SCR catalyst, comparing the mass of the accumulated urea deposit with a deposit upper threshold limit, and initiating an SCR regeneration event when the mass of the accumulated urea deposit is greater than the deposit upper threshold limit. The operations of the computer program product can further include determining an amount of $NH_3$ passing through the SCR catalyst downstream of the urea deposit, comparing the amount of $NH_3$ passing through the SCR catalyst with an $NH_3$ regeneration threshold limit, and terminating the SCR regeneration event when the level of $NH_3$ passing through the SCR catalyst is less than the SCR $NH_3$ regeneration threshold.

Reference throughout this specification to features, advantages, or similar language does not imply that all of the features and advantages that may be realized with the subject matter of the present disclosure should be or are in any single embodiment. Rather, language referring to the features and advantages is understood to mean that a specific feature, advantage, or characteristic described in connection with an embodiment is included in at least one embodiment of the present disclosure. Thus, discussion of the features and advantages, and similar language, throughout this specification may, but do not necessarily, refer to the same embodiment.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Internal Combustion Engine System

Figure 1:
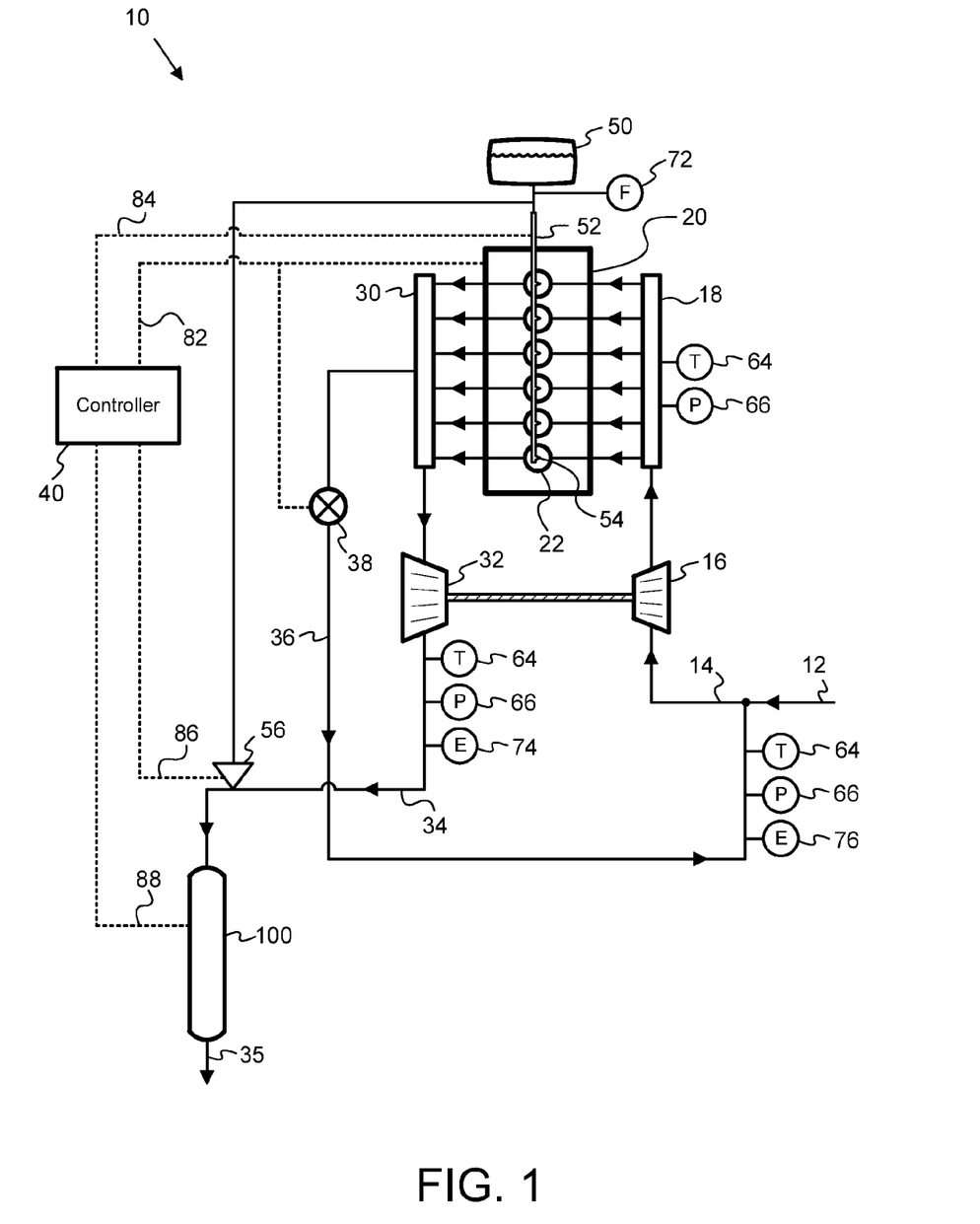
FIG. 1 is a schematic diagram of an engine system having an internal combustion engine and an exhaust after-treatment system, in accordance with one representative embodiment.

FIG. 1 depicts one embodiment of an engine system 10. The main components of the engine system 10 include an internal combustion engine 20 and an exhaust gas after-treatment system 100 in exhaust gas-receiving communication with the engine 20. The internal combustion engine 20 can be a compression-ignited internal combustion engine, such as a diesel fueled engine, or a spark-ignited internal combustion engine, such as a gasoline fueled engine operated lean. On the intake side, the engine system 10 can include an air inlet 12, inlet piping 14, a turbocharger compressor 16, and an intake manifold 18. The intake manifold 18 includes an outlet operatively coupled to compression chambers 22 of the internal combustion engine 20 for introducing air into the compression chambers 22.

Within the internal combustion engine 20, the air from the atmosphere is combined with fuel to power the engine. The fuel comes from the fuel tank 50 through a fuel delivery system including, in one embodiment, a fuel pump and common rail 52 to the fuel injectors 54, which inject fuel into the combustion chambers 22 of the engine 20. Fuel injection timing can be controlled by the controller 40 via a fuel injector control signal 84.

Combustion of the fuel and air in the compression chambers 22 produces exhaust gas that is operatively vented to an exhaust manifold 30. From the exhaust manifold 30, a portion of the exhaust gas may be used to power the turbocharger turbine 32. The turbocharger turbine 32 drives the turbocharger compressor 16, which may compress at least some of the air entering the air inlet 12 before directing it to the intake manifold 18 and into the compression chambers of the engine 20.

For the purposes of altering the combustion properties of the engine 20, a portion of the exhaust gas may bypass the turbocharger turbine 32 and be re-circulated to the engine 20 via an exhaust gas recirculation (EGR) line 36 and back to the inlet piping 14. In one embodiment, an EGR valve 38 is actuated to divert an amount of exhaust gas corresponding to a proportion set by a controller 40 via an EGR control signal.

The portion of the exhaust gas which is not re-circulated to the engine 110 via the EGR line 36 is destined for expulsion from the engine system 10 into the atmosphere. Thus, the exhaust gas stream flows from the exhaust manifold 30 or turbocharger turbine 32, through the exhaust piping 34, and through the exhaust gas after-treatment system 100 prior to being vented into the atmosphere through tailpipe 35. The exhaust gas after-treatment system 100 is configured to remove various chemical compounds and particulate emissions present in the exhaust gas received from the exhaust manifold 30. Specifically, the exhaust gas treated in the exhaust gas after-treatment system 100 contains significantly fewer pollutants, such as unburned hydrocarbons, CO, diesel particulate matter, and $NO_x$, than untreated exhaust gas.

Various sensors, such as temperature sensors 64, pressure sensors 66, fuel sensor 72, exhaust gas flow sensors 74, 76 and the like, may be strategically disposed throughout the engine system 10 and may be in communication with the controller 40 to monitor operating conditions of the engine system 10. In one embodiment, the fuel sensor 72 senses the amount of fuel consumed by the engine, and the exhaust gas flow sensor 74 senses the rate at which the exhaust gas is flowing towards exhaust gas after-treatment system 100.

Exhaust Gas After-Treatment System

Figure 2:
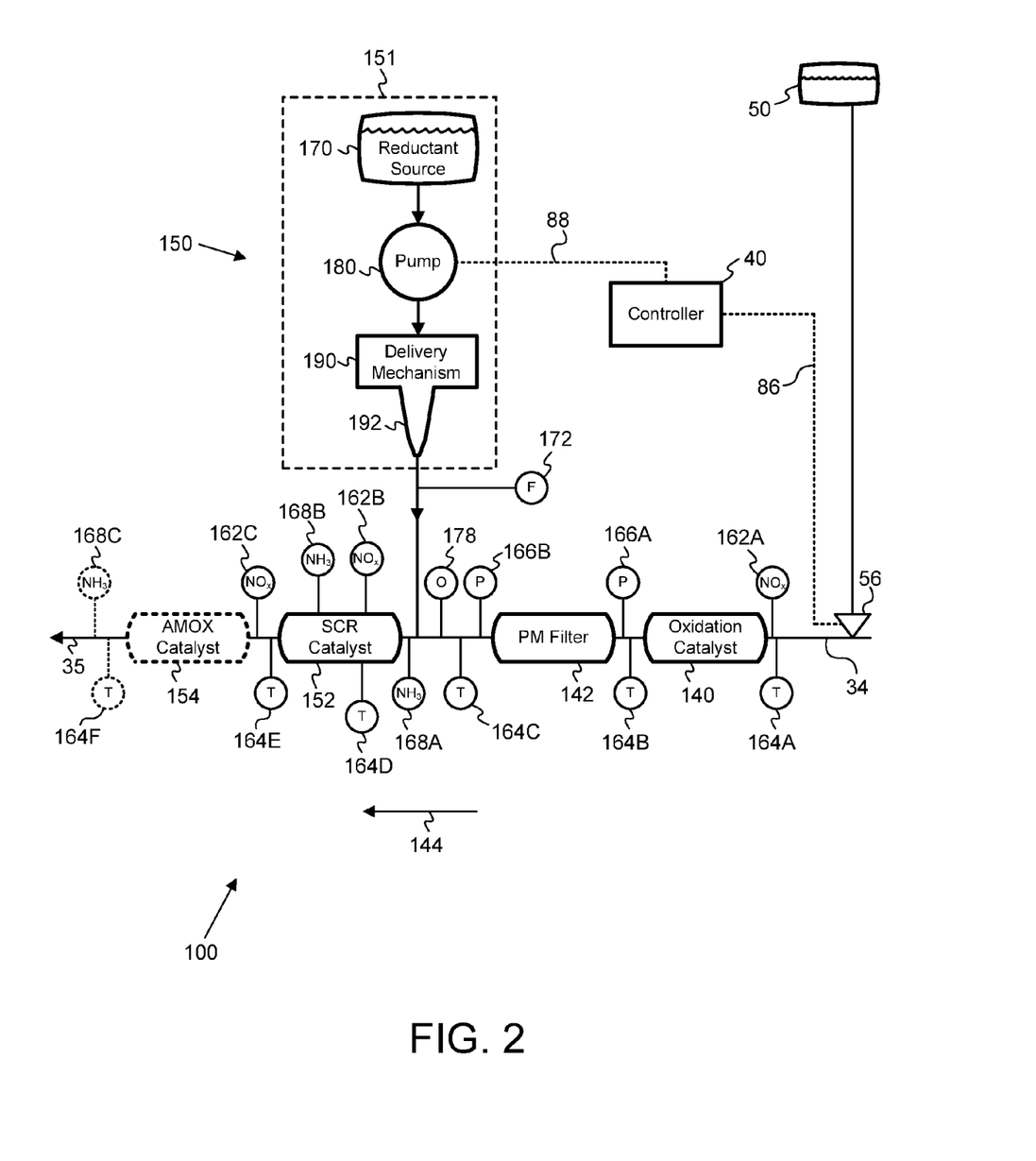
FIG. 2 is a schematic diagram of the exhaust after-treatment system of FIG. 1, in accordance with one representative embodiment.

Referring now to FIG. 2, the exhaust gas after-treatment system 100 includes the controller 40, an oxidation catalyst 140, a particulate matter (PM) filter 142, a selective catalytic reduction "SCR" system 150 having a reductant delivery system 151 and an SCR catalyst 152, and an optional ammonia oxidation (AMOX) catalyst 154. In an exhaust flow direction, as indicated by directional arrow 144, exhaust may flow from the exhaust piping 36, through the oxidation catalyst 140, through the PM filter 142, through the SCR catalyst 152, through the AMOX catalyst 160, and then be expelled into the atmosphere through tailpipe 35. Thus, in the illustrated embodiment the PM filter 142 is positioned downstream of the oxidation catalyst 140, the SCR catalyst 152 is positioned downstream of the PM filter 142, and the AMOX catalyst 154 is positioned downstream of the SCR catalyst 152. However, other arrangements of the components of the exhaust gas after-treatment system 100 are also possible.

The oxidation catalyst 140 can be any of various flow-through designs known in the art, including diesel oxidation catalysts (DOC). Generally, the oxidation catalyst 140 is configured to oxidize at least some particulate matter, e.g., the soluble organic fraction of soot, in the exhaust and reduce unburned hydrocarbons and CO in the exhaust to less environmentally harmful compounds. For example, the oxidation catalyst 140 may sufficiently reduce the hydrocarbon and CO concentrations in the exhaust to meet the requisite emissions standards for those components of the exhaust gas.

In addition to treating the hydrocarbon and CO concentrations in the exhaust gas, the oxidation catalyst 140 can also be used in the controlled regeneration of the PM filter 142 and the SCR catalyst 152. This can be accomplished through the injection, or dosing, of unburned hydrocarbons "UHC" into the exhaust gas upstream of the oxidation catalyst 140. Upon contact with the oxidation catalyst 140, the UHC undergoes an exothermic oxidation reaction which leads to an increase in the temperature of the exhaust gas exiting the oxidation catalyst 140 and subsequently entering the PM filter 142 and/or SCR catalyst 152. The amount of UHC added to the exhaust gas is selected to achieve the desired temperature increase or target controlled regeneration temperature.

The engine system 10 of FIG. 1 can use an internal fuel dosing strategy, an external fuel dosing strategy, or a combination of internal and external fuel dosing strategies to introduce the desired amount of UHC into the primary exhaust gas stream prior to the oxidation catalyst 140. In an internal fuel dosing strategy, for instance, the UHC can be derived from extra fuel that is injected into the compression cylinders 22 of the engine 20 after the combustion events having taken place within the cylinder. The UHC are then carried out of the engine 20 along with the products of combustion to the exhaust manifold 30, and from there to the exhaust gas after-treatment system 100. The internal fuel injection approach can be the same as or similar to the approach described in U.S. Pat. No. 8,061,127, which is incorporated herein by reference.

In an external fuel dosing strategy, the UHC can be derived from extra fuel that is injected via a separate fuel injector 56 directly into the exhaust piping 34 upstream of the exhaust gas after-treatment system 100. The fuel injector 56 may be in fluid communication with the fuel source 50 and selectively activated as needed based on an external fuel dosing control signal 86 received from the controller 40. The external fuel injection approach can be the same as or similar to the approach described in U.S. Pat. No. 7,263,825, which is incorporated herein by reference. Although fuel dosing strategies have been described as types of thermal management levers for increasing the exhaust temperature, other levers can be used, such as exhaust heaters and internal engine combustion strategies.

The PM filter 142 can be any of various flow-through designs known in the art, including diesel particulate filters (DPF), and configured to reduce particulate matter concentrations, e.g., soot and ash, in the exhaust gas to meet requisite emission standards. In addition, the exhaust gas after-treatment system 100 can further include a variety of sensors surrounding the PM filter 142 and which are electrically coupled to the controller 40. The sensors can include exhaust gas temperature sensors 164B, 164C and exhaust gas pressure sensors 166A, 166B.

Based on the input from these sensors, the controller 40 can monitor various properties of the exhaust gas entering and leaving the PM filter 142 so as to ascertain the current status of the PM filter 142. These exhaust gas properties may include the change in pressure across the PM filter 142 and the temperature of the exhaust gas stream entering and leaving the PM filter 142. Using these values, the controller 40 can monitor the temperature, timing, duration and effectiveness of filter regeneration events. In some implementations, the PM filter 142 and associated sensors and control system 40 is similar to, or the same as, the respective particulate filters, sensors, and control systems described in U.S. Pat. Nos. 7,231,291, 7,562,524, 7,478,527, and 7,587,892, each of which is incorporated herein by reference.

The SCR system 150 includes a reductant delivery system 151 comprising a reductant source 170, pump 180 and delivery mechanism 190. The reductant source 170 can be a container or tank capable of retaining a reductant, such as, for example, ammonia ($NH_3$), urea, diesel fuel, or diesel oil. The reductant source 170 is in reductant supplying communication with the pump 180, which is configured to pump reductant from the reductant source to the delivery mechanism 190. The delivery mechanism 190 can include a reductant injector schematically shown at 192 positioned upstream of the SCR catalyst 152. The injector is selectively controllable to inject reductant directly into the exhaust gas stream prior to entering the SCR catalyst 152.

In some embodiments, the reductant can either be ammonia or urea, which decomposes to produce ammonia. As will be described in more detail below, in these embodiments, the ammonia reacts with $NO_x$ in the presence of the SCR catalyst 152 to reduce the $NO_x$ to less harmful emissions, such as $N_2$ and $H_2O$. The SCR catalyst 152 can be any of various catalysts known in the art. For example, in some implementations, the SCR catalyst 152 is a vanadium-based catalyst, and in other implementations, the SCR catalyst is a zeolite-based catalyst, such as a Cu-Zeolite or a Fe-Zeolite catalyst. In one representative embodiment, the reductant is aqueous urea and the SCR catalyst 152 is a zeolite-based catalyst.

The AMOX catalyst 154 can be any of various flow-through catalysts configured to react with ammonia to produce mainly nitrogen. Generally, the AMOX catalyst 154 is utilized to remove any ammonia that has slipped through or exited the SCR catalyst 152 without reacting with $NO_x$ in the exhaust. In certain instances, the after-treatment system 100 can be operable with or without an AMOX catalyst. Further, although the AMOX catalyst 154 is shown as a separate unit from the SCR catalyst 152, in some implementations, the AMOX catalyst can be integrated with the SCR catalyst, e.g., the AMOX catalyst and the SCR catalyst can be located within the same housing.

The embodiment of the exhaust after-treatment system 100 illustrated in FIG. 2 incorporates multiple $NO_x$ sensors which measure the reduction of $NO_x$ throughout the exhaust treatment process. These include $NO_x$ sensor 162A upstream of the oxidation catalyst 140, $NO_x$ sensor 162B embedded within the SCR catalyst 152, $NO_x$ sensor 162C intermediate the SCR catalyst 152 and the AMOX catalyst 154, and $NO_x$ sensor 162D downstream of the AMOX catalyst 154.

The exhaust after-treatment system 100 can also utilize various sensors surrounding or even installed within the SCR catalyst and the AMOX catalyst, including temperature sensors 164D-164F, oxygen sensor 178, $NH_3$ sensors 168A-168C, and the like. As shown, $NH_3$ sensor 166A is located upstream of the SCR catalyst 152, $NH_3$ sensor 166B is embedded within the SCR catalyst 152, and $NH_3$ sensor 166C downstream of the AMOX catalyst 154. In some cases an $NO_x$ sensor and an $NH_3$ sensor may be combined into a dual ammonia-$NO_x$ sensors (not shown). The various sensors may be in electrical communication with the controller 40 to allow the controller monitor the operating conditions of the exhaust after-treatment system 100 of the engine system 10.

Although the exhaust after-treatment system 100 shown includes one of an oxidation catalyst 140, PM filter 142, SCR catalyst 152, and AMOX catalyst 154 positioned in specific locations relative to each other along the exhaust flow path, in other embodiments, the exhaust after-treatment system may include more than one of any of the various catalysts positioned in any of various positions relative to each other along the exhaust flow path as desired. Further, although the oxidation catalyst 140 and AMOX catalyst 154 are non-selective catalysts, in some embodiments, the oxidation and AMOX catalysts can be selective catalysts.

The controller 40 controls the operation of the engine system 10 and associated sub-systems, such as the internal combustion engine 20 and the exhaust gas after-treatment system 100. The controller 40 is depicted in FIGS. 1 and 2 as a single physical unit, but can include two or more physically separated units or components in some embodiments if desired. Generally, the controller 40 receives multiple inputs, processes the inputs, and transmits multiple outputs. The multiple inputs may include sensed measurements from the sensors and various user inputs. The inputs are processed by the controller 40 using various algorithms, stored data, and other inputs to update the stored data and/or generate output values. The generated output values and/or commands are transmitted to other components of the controller and/or to one or more elements of the engine system 100 to control the system to achieve desired results, and more specifically, achieve desired exhaust gas emissions.

For example, the operating conditions of the internal combustion engine 20 and the exhaust gas after-treatment system 100 can be ascertained from any of the sensors or from the controller's 40 commands to the engine regarding the fraction of exhaust gas recirculation, injection timing, and the like. In one embodiment, information is gathered regarding, for example, fuel rate, engine speed, engine load, the timing at which fuel injection timing is advanced or retarded (SOI, or start of injection), the fraction of exhaust gas recirculation, driving conditions, exhaust flow rate, the amount of $O_2$, $NO_2$, and $NH_3$ and in the exhaust gas, exhaust gas temperatures and pressures at various locations within the exhaust gas after-treatment system 100, and the elapsed time since one or more earlier events, such as a PM filter regeneration event or an SCR catalyst regeneration event.

The controller 40 includes various modules for controlling the operation of the engine system 10. For example, the controller 40 includes one or more modules for controlling the operation of the internal combustion engine 20. The controller 40 also includes one or more modules for controlling the regeneration of the PM filter 142 as described above. The controller 40 further includes one or more modules for controlling the operation and regeneration of the SCR system 150. Additionally, in the event the oxidation catalyst 140 and AMOX catalyst 154 are selectively controllable, the controller 40 can include one or more modules for controlling the operation of the respective oxidation and AMOX catalysts.

Control System

Figure 3:
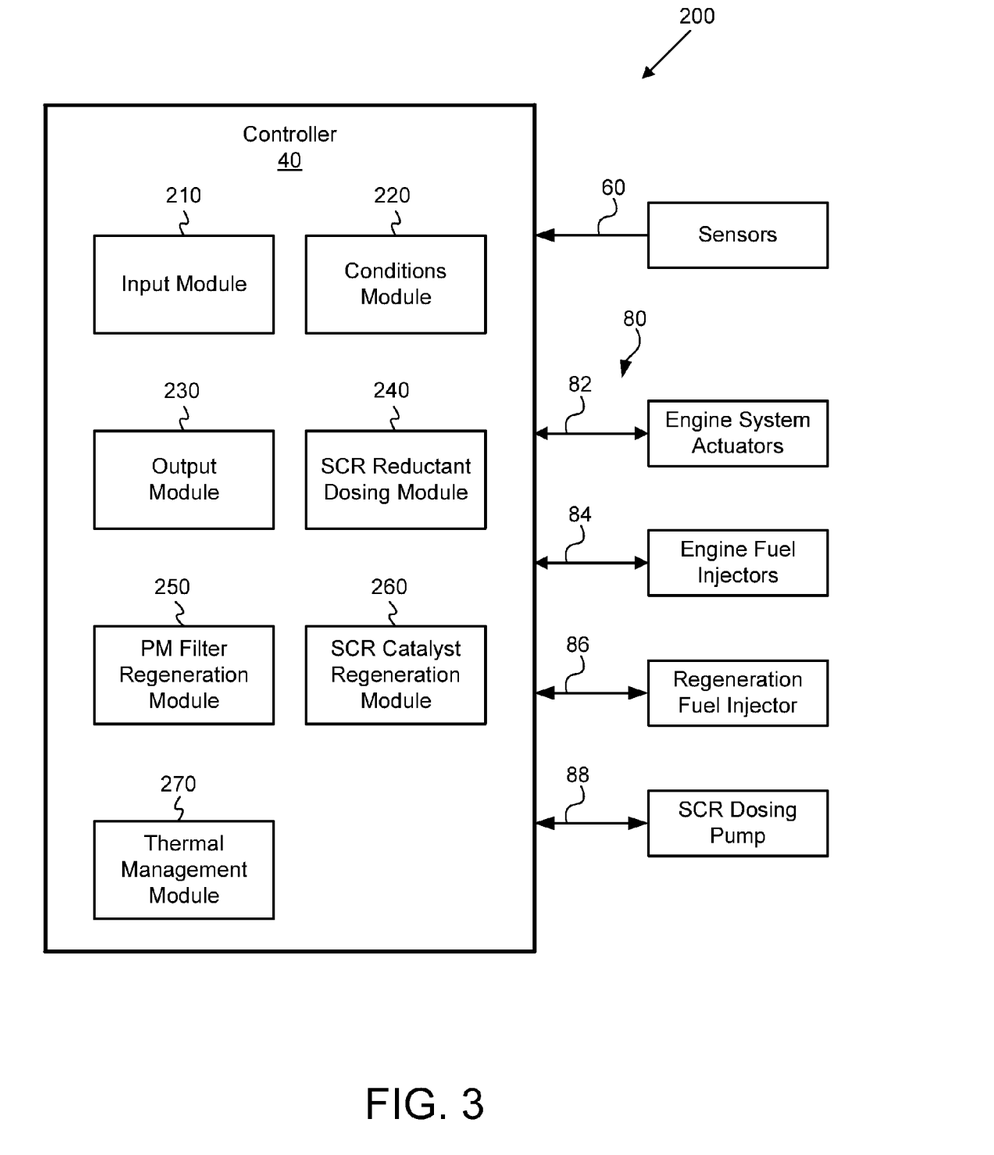
FIG. 3 is a schematic block diagram of a controller of the engine system of FIG. 1, in accordance with one representative embodiment.

FIG. 3 depicts a control system 200, according to one representative embodiment. The control system 200 includes the controller 40, inputs 60 from a variety of engine system and exhaust system sensors, and command outputs 80 to a variety engine system and exhaust system actuators. The control system inputs 60 may include sensor signals from the temperature sensors 64, pressure sensors 66, fuel sensor 72 and exhaust gas flow sensors 74 of FIG. 1. The control system inputs 60 may also include sensor signals from the $NO_x$ sensors 162A-162D, temperature sensors 164A-164F, pressure sensors 166A-166B, $NH_3$ sensors 168A-168C, fuel sensor 172, and oxygen sensor 178 of FIG. 2. Additional sensor inputs which are not specifically identified and described with reference to FIGS. 1-2 are also possible. The command outputs 80 may include, but are not limited to, one or more engine system actuator control signals 84, one or more engine fuel injector control signals 86, a regeneration fuel injector control signal 86, and an SCR dosing pump control signal 88. Furthermore, each of the control signals 82, 84, 86, 88 can include a feedback signal from the actuated component to the controller that is reflective of the current state or status of the actuated component.

The controller 40 includes various controller modules for controlling the operation of the engine system 10. For example, in the illustrated embodiment the controller 40 includes an input module 210, a conditions module 220, an output module 230, an SCR reductant dosing module 240, a PM filter regeneration module 250, an SCR catalyst regeneration module 260, and a thermal management module 270. While not specifically illustrated and described with reference to FIG. 3, the additional controller modules for conducting other control system functions are also possible and can be considered to fall within the scope of the present disclosure.

As is known in the art, the controller 40 and its various modular components may comprise processor, memory, and interface modules that may be fabricated of semiconductor gates on one or more semiconductor substrates. Each semiconductor substrate may be packaged in one or more semiconductor devices mounted on circuit cards. Connections between the modules may be through semiconductor metal layers, substrate-to-substrate wiring, or circuit card traces or wires connecting the semiconductor devices.

As mentioned above, the sensors of the engine system 10 are configured to determine, whether directly or indirectly, a plurality of conditions within the engine system 10, including but not limited to temperature, pressure, $NO_x$ concentration, exhaust gas flow rate and the like. Similarly, the actuators of the engine system 10 are any of various components that are selectively controlled or actuated to affect the operating conditions of the system, including but not limited to an exhaust throttle, an intake throttle, the EGR valve and the like, with the actuation of the engine fuel injectors, the regeneration fuel injector, and the SCR dosing pump being shown separately in FIG. 3.

The input module 210 is configured to receive sensor inputs 60 reflective of the conditions sensed by the various sensors, as well as actuator state inputs 80 from the engine system actuators, the engine and reductant fuel injectors, and the SCR dosing pump. The input module 210 can then provide corresponding inputs to the SCR reductant dosing module 230, the PM filter regeneration module 250, the SCR catalyst regeneration module 260, and the thermal management module 270. The conditions module 220 is configured to gather additional information regarding current conditions of the engine system 10, based on the conditions sensed by the sensors and/or other inputs including the command outputs 80 issued to the various system components by the controller 40. Via the command outputs 80, the output module 240 is configured to direct the engine system actuators, the engine fuel injectors, the SCR dosing pump, and the regeneration fuel injector according to the dosing and regeneration instructions generated by the SCR reductant dosing module 240, the PM filter regeneration module 250, the SCR catalyst regeneration module 260, and thermal management module 270.

Figure 4:
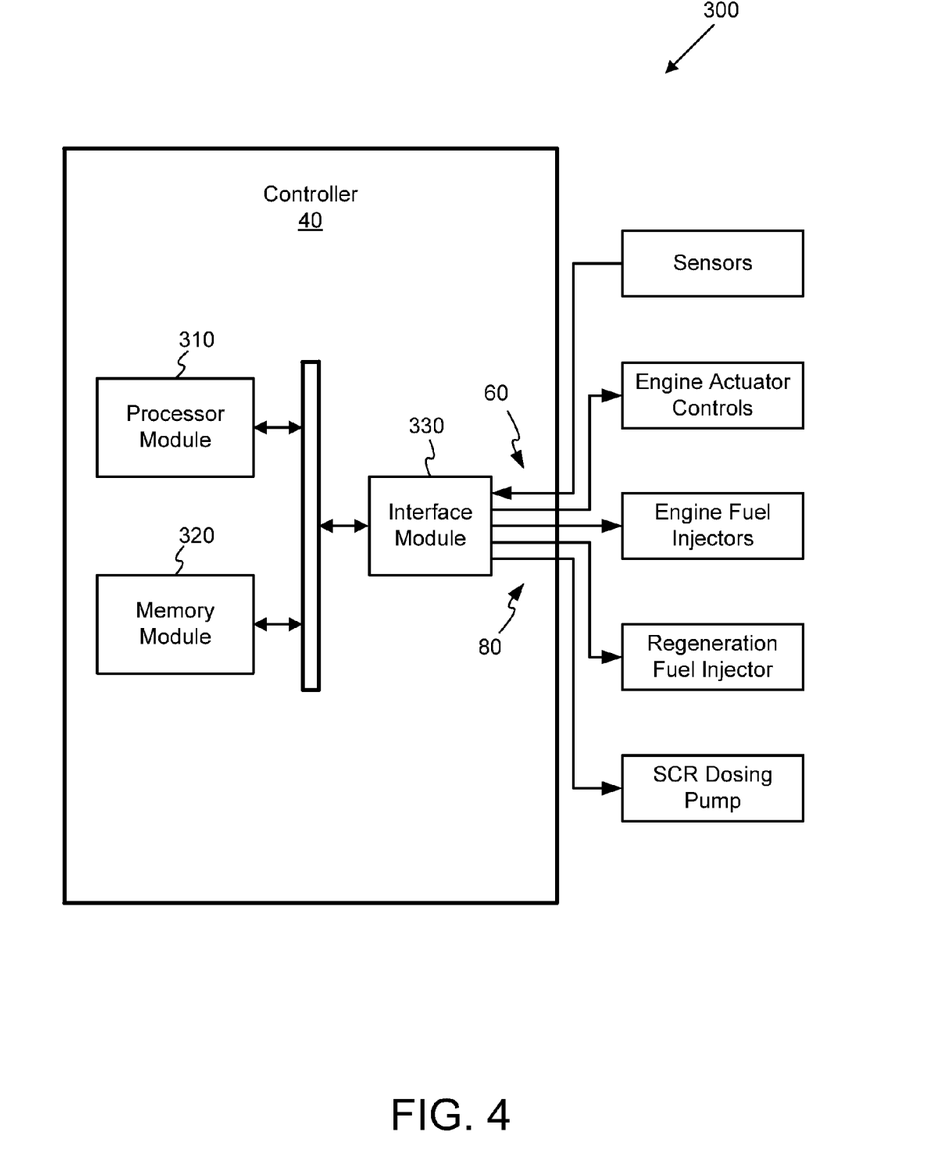
FIG. 4 is a schematic block diagram of a controller of the engine system of FIG. 1, in accordance with another representative embodiment.

FIG. 4 depicts another representative embodiment of the control system 300, which control system 300 also includes the controller 40, the inputs 60 from the various sensors, and the command outputs 80 to the various engine system and exhaust system actuators. In this embodiment, the controller 40 is depicted as comprising a processor module 310, memory module 320, and interface module 330. The processor module 310, memory module 320, and interface module 330 may be fabricated of semiconductor gates on one or more semiconductor substrates. Each semiconductor substrate may be packaged in one or more semiconductor devices mounted on circuit cards. Connections between the processor module 310, the memory module 320, and the interface module 330 may be through semiconductor metal layers, substrate to substrate wiring, or circuit card traces or wires connecting the semiconductor devices.

The memory module 320 stores software instructions and data comprising one or more software processes. The processor module 310 executes the software processes as is known to those skilled in the art. In the illustrated embodiment of FIG. 4, the processor module 310 can execute one or more software processes carried out by the conditions module 220, the SCR reductant dosing module 240, the PM filter regeneration module 250, the SCR catalyst regeneration module 260, and the thermal management module 270 of FIG. 3.

The processor module 310 may communicate with and control external devices and sensors, such as the sensors, the engine system actuators, the engine and reductant fuel injectors, and the SCR reductant dosing pump through the interface module 330. For example, the sensors may include pressure sensors 156A and 156B (see, e.g., FIG. 2) that communicate analog signals representing the pressure values upstream and downstream of the PM filter 242 to the interface module 330. The interface module 330 may periodically convert the analog signals to a digital value and communicate the digital values to the processor module 310.

The interface module 330 may also receive one or more digital signals through a dedicated digital interface, a serial digital bus communicating a plurality of digital values, or the like. For instance, the sensors may include one or more temperature sensors 64 (see, e.g., FIG. 1) that communicate a digital temperature value to the interface module 330. The interface module 330 may periodically communicate the digital temperature value to the processor module 310. In one embodiment, the interface module 330 executes one or more communication processes carried out by the input module 210 and output module 230 of FIG. 3.

The processor module 310 may store digital values such as the pressure value and the temperature value in the memory module 320. In addition, the processor module 310 may employ the digital values in one or more calculations including calculations carried out by the various modules of the controller 40. Although the above description was limited to pressure and temperature sensors, the interface module 330 can interface with any of the various sensors of the engine system 10 and the exhaust after-treatment system 100 to receive detected values for any of various sensed characteristics of the system.

SCR Reductant Dosing Module

Referring back to FIGS. 2 and 3, the SCR reductant dosing module 240 is operable to determine the amount of reductant which is required to be pumped into the exhaust after-treatment system 100 so as to reduce or substantially eliminate the $NO_x$ components in the exhaust gas stream. The SCR reductant dosing module 240 can then direct the output module 230 to output a command signal 88 to the reductant delivery system 151. The command signal 88 activates the reductant pump 180 to draw reductant from the reductant source 170 for injection via the delivery mechanism 190 into the exhaust after-treatment system 100 upstream of the SCR catalyst.

In some implementations, the SCR reductant dosing module 240 can be the same as or similar to the combination of control modules described in U.S. Pat. No. 8,109,079, U.S. patent application Ser. No. 12/433,586, and U.S. Pat. No. 8,141,340, which are incorporated herein by reference.

PM Filter Regeneration Module

The PM filter regeneration module 250 is operable to determine the degree of build-up of soot and ash in the PM filter 142 and to initiate a PM filter regeneration event, as described above. The PM filter regeneration module 250 can communicate a regeneration command to the thermal management module 270 that may include the desired PM filter inlet exhaust gas temperature, as measured by temperature sensor 164B.

In some implementations, the PM filter regeneration module 250 can be the same as or similar to the combination of control modules described in U.S. Pat. No. 7,263,825 and U.S. patent application Ser. No. 12/111,831, as described above.

Thermal Management Module

Referring back to FIGS. 1-3, the thermal management module 270 is operable to implement one or more unburned hydrocarbon (UHC) dosing strategies based on a regeneration command received from the PM filter regeneration module or the SCR catalyst regeneration module. The regeneration command may include, at least in part, the desired PM filter inlet exhaust gas temperature received from the PM filter regeneration module 250, or a desired SCR catalyst inlet exhaust gas temperature received from the SCR catalyst regeneration module 260.

Based on the desired temperature included in the regeneration command and the operating conditions of the engine 20 received from the conditions module 220, the thermal management module 270 can then direct the output module 230 to output a command signal 84 to the engine fuel injectors 54 to initiate an internal fuel dosing event, or to output a command signal 86 to the regeneration fuel injector 56 to initiate an external fuel dosing event. In the case of the external fuel dosing approach, the command signal 86 activates the regeneration fuel injector 56 to cause UHC from the fuel source 50 to be injected into the exhaust piping 34 or the exhaust after-treatment system 100 upstream of the oxidation catalyst 140.

SCR Catalyst Regeneration Module

The SCR catalyst regeneration module 260 is operable to determine the degree of build-up or amount of urea deposits in the SCR catalyst and to initiate an SCR catalyst regeneration event to remove all or a portion of the deposits, as described above. In the present embodiment, the SCR catalyst regeneration module 260 is configured to communicate an SCR catalyst regeneration command to the thermal management module 270. The SCR catalyst regeneration command may include the desired SCR catalyst inlet exhaust gas temperature, as measured by temperature sensors 164C or 164D.

As appreciated by one of skill in the art, the rate of urea deposit accumulation can vary substantially based on the temperature of the exhaust gas as it enters the SCR catalyst (e.g. which temperature variations are typically caused by the changing operating conditions of the internal combustion engine). Accordingly, the time interval between SCR regeneration events may also vary substantially. When the temperature of the exhaust gas drops below some lower temperature threshold (e.g., when the engine system is in a slow idle mode, for example), some of the vaporized urea can condense onto the interior surfaces of the SCR system piping and the SCR catalyst bed and crystalize into urea deposits, which can build over time. Raising the temperature of the exhaust gas to above some upper temperature threshold (e.g., such as during a SCR catalyst regeneration event) will cause the surface of the urea deposit(s) to begin to sublimate or decompose back into ammonia, which then continues through the SCR portion of the exhaust gas after-treatment system. It has been found that the temperature of the exhaust gas at the SCR catalyst inlet must remain elevated for an extended determinable period of time for a urea deposit of average mass to be completely decomposed into gaseous $NH_3$.

Figure 5:
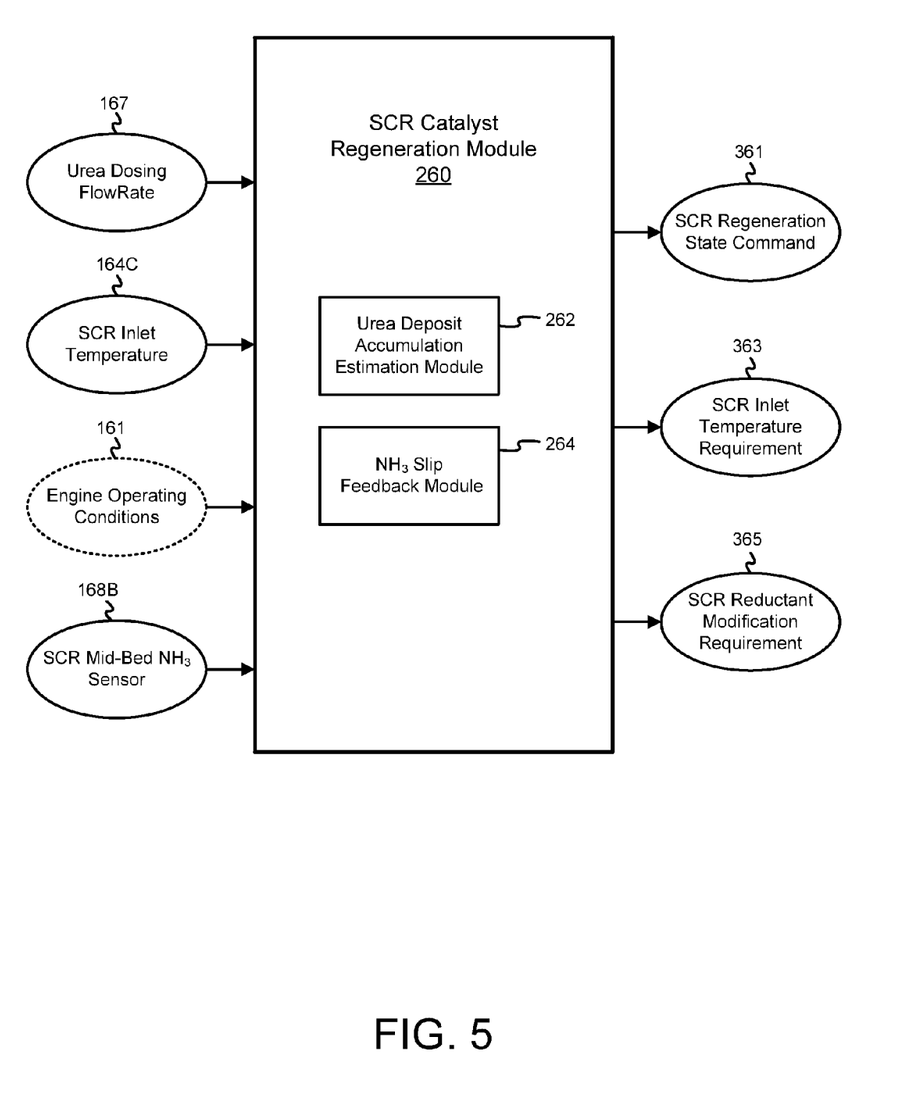
FIG. 5 is a schematic block diagram of an SCR catalyst regeneration module of the controller of FIG. 3, in accordance with one representative embodiment.

Referring to both FIGS. 2 and 5, the SCR catalyst regeneration module 260 includes a urea deposit accumulation estimation module 262 and an $NH_3$ slip feedback module 264. The urea deposit accumulation estimation module 262 is configured to determine the rate of urea deposit accumulation within the SCR system. The urea deposit accumulation estimation module 262 may utilize any of various technologies or methodologies for determining the rate of urea deposit accumulation. According to one implementation, the determination of the rate of urea deposit accumulation is based, at least in part, on the urea dosing rate of the reductant delivery system 151 and/or other aftertreatment operating conditions. The urea dosing rate can be measured directly by the reductant flow meter 172 or provided electronically by the SCR reductant dosing module 240.

To further refine its estimate for the rate of urea deposit accumulation, the urea deposit accumulation estimation module 262 may also utilize additional engine operating conditions 161, including, but not limited to, the exhaust flow rate of the exhaust gas stream (from exhaust flow sensor 74), SCR catalyst inlet $NO_x$ flow rate (from $NO_x$ sensor 162B), and SCR catalyst outlet $NO_x$ flow rate (from $NO_x$ sensor 162C). The inputs from each of the sensors can be passed to the urea deposit accumulation estimation module 262 via the conditions module 220.

The urea deposit accumulation estimation module 262 can apply the above sensor inputs to an electronic model of the SCR system and SCR piping to calculate the rate of urea deposit accumulation. Furthermore, the electronic model may be calibrated for the particular characteristics of the SCR system and piping based on experimental data. Once the rate of urea deposit accumulation has been calculated, the urea deposit accumulation estimation module 262 can then integrate the rate of urea deposit accumulation over the elapsed time interval from a previous SCR regeneration event to determine the accumulated mass of the urea deposit which is likely to be present within the SCR catalyst and SCR piping. Of course, in other implementations, other methods and techniques, which may utilize actual sensors, virtual sensors, models, and/or the like, for determining the accumulated mass of the urea deposit within the SCR system can be used.

When the estimated accumulated mass of the urea deposit reaches a predetermined urea deposit threshold limit, also referred to as the upper threshold limit, the SCR catalyst regeneration module 260 is configured to initiate an SCR catalyst regeneration event by communicating an SCR catalyst regeneration command to the thermal management module 270. The SCR catalyst regeneration command may include the desired elevated value for the SCR catalyst inlet exhaust gas temperature, as measured by temperature sensors 164C or 164D. In some implementations, the SCR catalyst regeneration command may also include a time period for which the SCR catalyst inlet exhaust gas is to be maintained at the elevated temperature, which time period may be measured by a digital clock included within the controller 40.

As stated above, the thermal management module 270 is configured to receive the SCR catalyst regeneration command and direct the output module 230 to generate a command signal that initiates either an internal fuel dosing event or an external fuel dosing regeneration event. When the unburned hydrocarbons (UHC) come into contact with the oxidation catalyst 140, the resulting exothermic reaction raises the temperature of the exhaust gas exiting the oxidation catalyst 140 and traveling downstream towards the SCR catalyst 152. Based upon simultaneous temperature measurements taken at temperature sensors 164C or 164D, the amount of UHC added to the exhaust gas can be selectively controlled by the thermal management module 270 to achieve and maintain the target SCR catalyst inlet exhaust gas temperature needed for regeneration.

When the temperature of the SCR inlet gas reaches the desired elevated value, the urea deposit will begin to sublimate and decompose back into ammonia, which then continues through the SCR catalyst towards the SCR mid-bed $NH_3$ sensor 168B. Generally, the amount of additional ammonia released by the decomposing urea deposit will be an order of magnitude greater than the amount of ammonia sensed by the SCR mid-bed $NH_3$ sensor 168B during normal reductant dosing operations.

As stated above, the SCR catalyst regeneration module 260 also includes an $NH_3$ slip feedback module 264, which monitors the ammonia measurement taken at the SCR mid-bed $NH_3$ sensor 168B to determine the flow rate of $NH_3$ passing through the SCR catalyst downstream of the urea deposit. The $NH_3$ slip feedback module 264 can then integrate the flow rate of $NH_3$ over the elapsed time interval from the initiation of the SCR regeneration event to determine the total amount of $NH_3$ passing through the SCR system downstream of the urea deposit.

If the total amount of ammonia reaching the SCR mid-med $NH_3$ sensor 168B reaches or exceeds an SCR $NH_3$ regeneration threshold, this indicates that a mass of urea deposit in the SCR piping and SCR catalyst has begun to decompose. Thus, the $NH_3$ slip feedback module 264 is configured to verify and confirm the presence of the urea deposit and to allow the SCR regeneration event to continue.

If, however, within a certain period of time after the initiation of the SCR regeneration event, the SCR mid-bed $NH_3$ sensor 168B fails to measure the amount of additional ammonia indicative of a decomposing urea deposit (e.g. the SCR $NH_3$ regeneration threshold), the SCR catalyst regeneration module 260 is configured to terminate the SCR regeneration event. This has the advantage of reducing the number of elevated heat cycles experienced by the SCR catalyst, which in turn decreases the wear and degradation of the SCR catalyst components. This also has the advantage of reducing the amount of additional fuel required by the internal combustion engine system to maintain its exhaust after-treatment system in good operating condition.

The SCR $NH_3$ regeneration threshold can be experimentally predetermined and customized to the specific characteristics of the internal combustion engine and the exhaust after-treatment system (e.g. type and size of the engine, type of SCR catalyst, etc.), with the values being entered into a look-up table included within the $NH_3$ slip feedback module 264. In other aspects, the SCR $NH_3$ regeneration threshold may be based on information received from the urea deposit accumulation estimation module 262 that is reflective of the current estimation for the mass of the accumulated urea deposit.

In one implementation, the total amount of ammonia reaching the SCR mid-bed $NH_3$ sensor 168B can include both the ammonia released from the urea deposit and the ammonia being dosed into the exhaust after-treatment system via the reductant dosing system 151. In another implementation, the amount of reductant being dosed into the exhaust after-treatment system can be reduced or stopped during the SCR regeneration event, so as to avoid creating excess ammonia slip which cannot be utilized by the portion of the SCR catalyst that is located further downstream from the SCR mid-bed $NH_3$ sensor 168B. In these circumstances the total amount of ammonia reaching the SCR mid-med $NH_3$ sensor 168B may be limited primarily to the ammonia released from the urea deposit. Although the $NH_3$ sensor 168B has been described as a mid-bed sensor, in other embodiments, the $NH_3$ sensor 168B can be located at any location downstream of the accumulated urea deposit and need not necessarily be located in a mid-bed position of the SCR catalyst.

Exemplary Method for Reducing NOx Emissions

Figure 6:
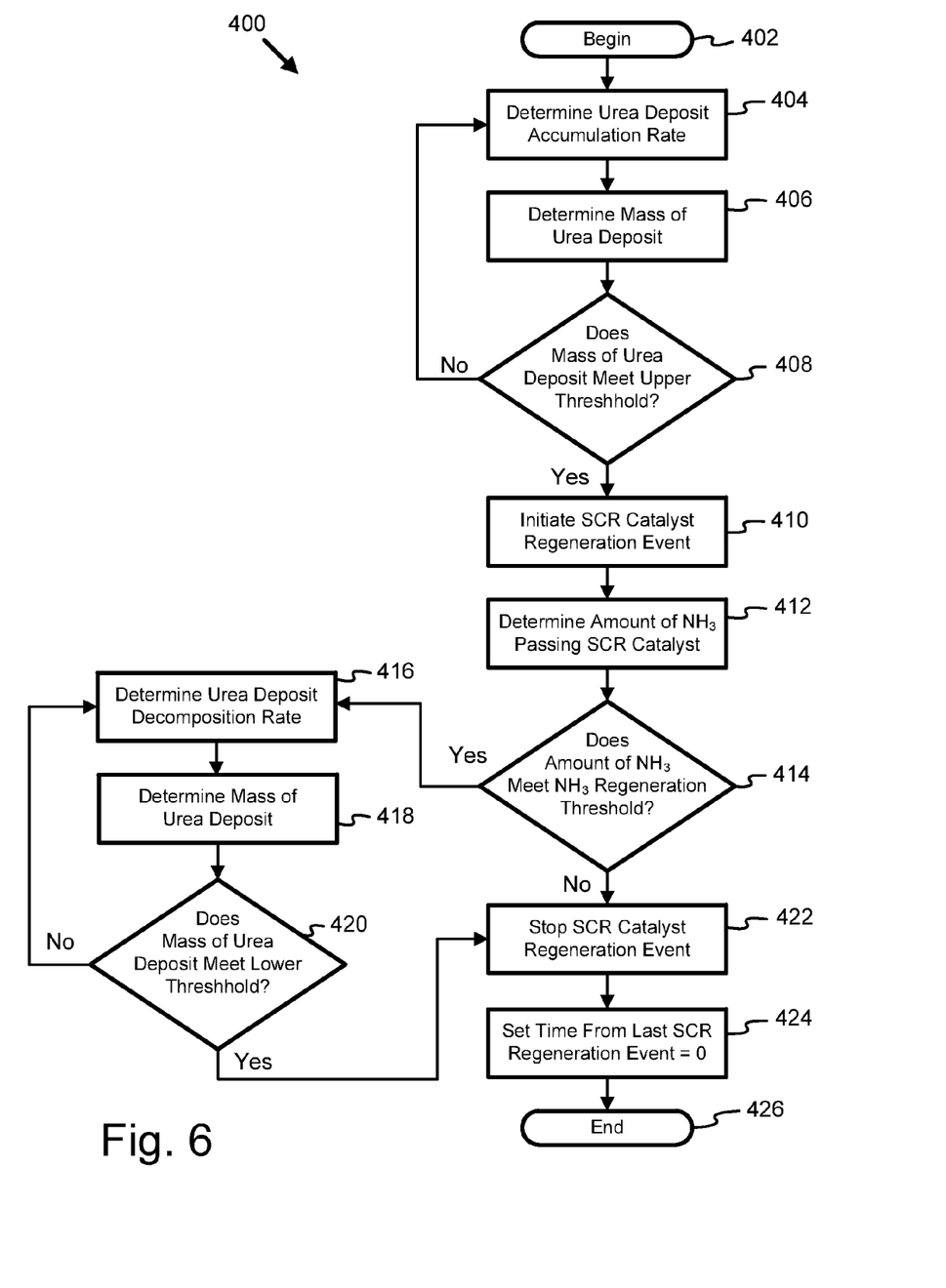
FIG. 6 is a schematic flow chart diagram of a control system operable to determine and remove an accumulation of urea deposits, in accordance with one representative embodiment.

Referring to FIG. 6, and according to one representative embodiment, a method 400 for mitigating a urea deposit within an SCR catalyst is shown. The method 400 starts at 402 and includes determining 404 a urea deposit accumulation rate. In some implementations, determining 404 the urea deposit accumulation rate includes operating the urea deposit accumulation estimation module 262 to calculate the instantaneous rate of urea deposition based on, at least in part, the temperature of the exhaust gas entering the SCR catalyst 152 and the dosing rate of the reductant delivery system 151 being inputted into an electronic model of the SCR system. In other implementations, the instantaneous rate of urea deposition can be based on other or additional factors as is known in the art. In some implementations the urea deposit accumulation estimation module 262 may also include current engine system operating conditions, such as the exhaust flow rate of the exhaust gas stream, the SCR catalyst inlet $NO_x$ flow rate, and SCR catalyst outlet $NO_x$ flow rate, to further refine its calculation for the rate of urea deposition. The inclusion of additional measured conditions and control parameters not specifically described herein into the calculation of the urea deposit accumulation rate is also possible.

The method 400 also includes determining 406 the accumulated mass of the urea deposit (which can be a first estimate of the accumulated mass in some implementations) likely to be present within the SCR catalyst 252 and SCR piping. In some implementations, determining 406 the accumulated mass of the urea deposit includes operating the urea deposit accumulation estimation module 262 to integrate the rate of urea deposit accumulation over the elapsed time interval from a previous SCR regeneration event to determine the accumulated mass of the urea deposit. Determining 406 the accumulated mass of the urea deposit can also be accomplished using other techniques and/or processes known in the art.

The method 400 also includes determining 408 whether or not the accumulated mass of the urea deposit meets a urea deposit threshold limit. If the accumulated mass does not meet the urea deposit threshold limit, the urea deposit accumulation estimation module 262 cycles back to the step of determining 404 the urea deposit accumulation rate. If the accumulated mass does meet the urea deposit threshold limit, the method 400 progresses to initiating 410 an SCR regeneration event. In some implementations, initiating 410 an SCR regeneration event includes causing the SCR catalyst regeneration module 260 to communicate an SCR catalyst regeneration command to the thermal management module 270. The SCR catalyst regeneration command may include the desired elevated value for the SCR catalyst inlet exhaust gas temperature.

After the SCR regeneration event has been initiated, the method 400 includes determining 412 the amount of $NH_3$ passing through the SCR catalyst 150 downstream of the urea deposit. In some implementations, determining 412 the amount of $NH_3$ passing through the SCR catalyst includes monitoring the level of $NH_3$ with the SCR mid-bed $NH_3$ sensor 168B and the $NH_3$ slip feedback module 264. Using the $NH_3$ sensor located at the mid-bed location of the SCR catalyst has the advantage of capturing the level of $NH_3$ before it has had a chance to be completely utilized in the $NO_x$ reduction reaction or captured by the SCR catalyst for storage. This allows for a more accurate indication of the mass of the urea deposit, which information can be applied in future calculations. However, it also possible to monitor the level of $NH_3$ which has slipped completely through the SCR catalyst using a sensor positioned further below or downstream from the SCR catalyst, such as $NH_3$ sensor 168C.

In addition, determining 412 the amount of $NH_3$ below or downstream of the urea deposit can further include determining a rate of $NH_3$ passing through the SCR system downstream of the urea deposit, determining a time period which has elapsed from the initiation of the SCR regeneration event, and integrating the rate of $NH_3$ passing through the SCR system over the time period since the initiation of SCR regeneration event to calculate the amount of $NH_3$ passing through the SCR system.

The method 400 also includes determining 414 whether or not the amount of $NH_3$ passing through the SCR catalyst downstream of the urea deposit meets the SCR $NH_3$ regeneration threshold limit. If the $NH_3$ level downstream of the urea deposit does not meet the SCR $NH_3$ regeneration threshold limit, the SCR catalyst regeneration module 260 is configured to terminate or stop 422 the SCR regeneration event and to direct the controller 40 to return to normal exhaust after-treatment operation. Moreover, if the measured amount of $NH_3$ does not meet the SCR $NH_3$ regeneration threshold, this may indicate that the value for the accumulated mass of the urea deposit calculated by the urea deposit accumulation estimation module 262 was inaccurate, and the further adjustments to the estimation process may be necessary.

If the amount of $NH_3$ passing through the SCR catalyst does meet the SCR $NH_3$ regeneration threshold limit, the method 400 includes completing the SCR regeneration event by allowing the thermal management module 270 to maintain the desired elevated value for the SCR catalyst inlet exhaust gas temperature until it has been determined that the accumulated mass of the urea deposit has been decomposed to less than a urea deposit lower threshold limit. This includes determining 416 a urea deposit decomposition rate, which in some implementations includes operating the urea deposit accumulation estimation module 262 to calculate the instantaneous rate of urea decomposition based on, at least in part, the elevated temperature of the exhaust gas entering the SCR catalyst 152.

Under these circumstances, the method 400 also includes determining 418 the reduction in the accumulated mass of the urea deposit (which can include determining a second estimate of the accumulated mass of the urea deposit). In some implementations, determining 418 the reduction of the urea deposit (which can be used to determine the mass of the urea deposit after an SCR catalyst regeneration event has started) includes operating the urea deposit accumulation estimation module 262 to integrate the rate of urea deposit decomposition over the elapsed time interval from the initiation of the SCR regeneration event to determine the mass of the decomposing urea deposit. Accordingly, the method for determining the mass of the urea deposit at 406 before SCR catalyst regeneration has begun (e.g., at a first time period) can be the same as or different than the method for determining the mass of the urea deposit at 418 after the SCR catalyst regeneration has begun (e.g., at a second time period after the first time period).

The method 400 also includes determining 420 whether or not the accumulated mass of the urea deposit meets a urea deposit lower threshold limit. If the accumulated mass does not meet the urea deposit lower threshold limit, the SCR regeneration event continues and the urea deposit accumulation estimation module 262 cycles back to the step of determining 416 the urea deposit decomposition rate. If the accumulated mass does meet the urea deposit lower threshold limit, the method 400 progresses to terminating 422 the SCR regeneration event.

Alternatively, the method 400 can include completing the SCR regeneration event by allowing the thermal management module 270 to maintain the desired elevated value for the SCR catalyst inlet exhaust gas temperature for a predetermined period of time. In one implementation the predetermined period of time may be a fixed period of time stored within the thermal management module 270. In another implementation the predetermined period of time may be an adjustable time period proscribed in the SCR catalyst regeneration command. Allowing the thermal management module 270 to maintain the desired elevated temperature value at the SCR catalyst inlet for the predetermined period of time can ensure that the urea deposit will be completely decomposed by the end of the SCR regeneration event.

Whether the SCR regeneration event is allowed to complete normally or is terminated early, the method 400 concludes with setting 424 the time from the last SCR regeneration event to zero prior to ending the method at 426. This step may be taken so that the next cycle of the method 400 for mitigating a urea deposit within the SCR catalyst may start with an updated time reference. In some implementations, setting 424 the time from the last SCR regeneration event to zero may be accomplished by clearing memory registers in the processor module 310 or memory module 320 of the controller 40 (see, e.g., FIG. 4).

The schematic flow chart diagrams and method schematic diagrams described above are generally set forth as logical flow chart diagrams. As such, the depicted order and labeled steps are indicative of representative embodiments. Other steps, orderings and methods may be conceived that are equivalent in function, logic, or effect to one or more steps, or portions thereof, of the methods illustrated in the schematic diagrams. For example, the steps of setting 418 the time from the last SCR regeneration event to zero and setting 420 the value of accumulated mass of the urea deposit to zero may be performed at the beginning of the process, rather than at the end.

Additionally, the format and symbols employed are provided to explain the logical steps of the schematic diagrams and are understood not to limit the scope of the methods illustrated by the diagrams. Although various arrow types and line types may be employed in the schematic diagrams, they are understood not to limit the scope of the corresponding methods. Indeed, some arrows or other connectors may be used to indicate only the logical flow of a method. For instance, an arrow may indicate a waiting or monitoring period of unspecified duration between enumerated steps of a depicted method. Additionally, the order in which a particular method occurs may or may not strictly adhere to the order of the corresponding steps shown.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing.

In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method for mitigating a urea deposit within a selective catalytic reduction (SCR) system in exhaust receiving communication with an exhaust gas stream produced by an engine system, the exhaust gas stream flowing from an engine of the engine system to a tailpipe of the engine system, the method comprising:
   determining a mass of an accumulated urea deposit present within a SCR system, the SCR system including a SCR catalyst and SCR piping;
   comparing the mass of the accumulated urea deposit with a deposit upper threshold limit;
   initiating a SCR regeneration event when the mass of the accumulated urea deposit is greater than the deposit upper threshold limit;
   determining an amount of $NH_3$ passing through the SCR system downstream of the urea deposit;
   comparing the amount of $NH_3$ passing through the SCR system with an $NH_3$ regeneration threshold limit; and
   terminating the SCR regeneration event when the amount of $NH_3$ passing through the SCR system is less than the SCR $NH_3$ regeneration threshold, the SCR $NH_3$ regeneration threshold based on a decomposition rate of the mass of the accumulated urea deposit, the decomposition rate based on an exhaust gas temperature.

2. The method of claim 1, wherein determining the mass of an accumulated urea deposit comprises:
   determining a rate of urea deposit accumulation within the SCR system;
   determining a first time period, the first time period being the time elapsed from a previous SCR regeneration event; and
   integrating the rate of urea deposit accumulation within the SCR system over the first time period to calculate the mass of the accumulated urea deposit.

3. The method of claim 1, wherein determining the amount of NH3 passing through the SCR system downstream of the urea deposit comprises:
   determining a flow rate of $NH_3$ passing through the SCR system downstream of the urea deposit;
   determining a second time period, the second time period being the time elapsed from the initiation of the SCR regeneration event; and
   integrating the rate of $NH_3$ passing through the SCR system over the second time period to calculate the amount of $NH_3$ passing through the SCR system.

4. The method of claim 3, further comprising measuring the flow rate of $NH_3$ passing through the SCR system with a virtual $NH_3$ sensor.

5. The method of claim 3, further comprising measuring the flow rate of $NH_3$ passing through the SCR system with an $NH_3$ sensor positioned downstream of the urea deposit.

6. The method of claim 5, wherein the $NH_3$ sensor is a SCR catalyst $NH_3$ mid-bed sensor.

7. A method for mitigating a urea deposit within a selective catalytic reduction (SCR) system in exhaust receiving communication with an exhaust gas stream produced by an engine system, the exhaust gas stream flowing from an engine of the engine system to a tailpipe of the engine system, the method comprising:
   determining a mass of an accumulated urea deposit present within the SCR system, the SCR system including a SCR catalyst and SCR piping upstream of the SCR catalyst;
   comparing the mass of the accumulated urea deposit with a deposit upper threshold limit;
   initiating a SCR regeneration event when the mass of the accumulated urea deposit is greater than the deposit upper threshold limit;
   determining an amount of $NH_3$ passing through the SCR catalyst downstream of the urea deposit;
   comparing the amount of $NH_3$ passing through the SCR catalyst with an $NH_3$ regeneration threshold limit;
   maintaining the SCR regeneration event when the level of $NH_3$ passing through the SCR catalyst is greater than the $NH_3$ regeneration threshold limit;
   comparing the mass of the accumulated urea deposit with a deposit lower threshold limit; and
   terminating the SCR regeneration event when the mass of the accumulated urea deposit is less than the deposit lower threshold limit, the deposit lower threshold limit based on a decomposition rate of the mass of the accumulated urea deposit, the decomposition rate based on an exhaust gas temperature.

8. The method of claim 7, wherein determining the mass of the accumulated urea deposit comprises:
   determining a rate of urea deposit accumulation within the SCR system;
   determining a first time period, the first time period being the time elapsed from a previous SCR regeneration event; and
   integrating the rate of urea deposit accumulation within the SCR system over the first time period to calculate the mass of the accumulated urea deposit.

9. The method of claim 7, wherein determining the amount of $NH_3$ passing through the SCR catalyst downstream of the urea deposit comprises:
   determining a flow rate of $NH_3$ passing through the SCR catalyst downstream of the urea deposit;
   determining a second time period, the second time period being the time elapsed from the initiation of the SCR regeneration event; and
   integrating the rate of $NH_3$ passing through the SCR catalyst over the second time period to calculate the amount of $NH_3$ passing through the SCR catalyst.

10. The method of claim 9, further comprising measuring the flow rate of $NH_3$ passing through the SCR catalyst downstream of the urea deposit with a virtual $NH_3$ sensor.

11. The method of claim 9, further comprising measuring the flow rate of $NH_3$ passing through the SCR catalyst downstream of the urea deposit with an $NH_3$ sensor positioned downstream of the urea deposit.

12. The method of claim 11, wherein determining the mass of the accumulated urea deposit comprises:
   determining a rate of urea deposit decomposition within the SCR system; and
   integrating the rate of urea deposit decomposition within the SCR system over the second time period to calculate the mass of the accumulated urea deposit.

* * * * *